US010716627B2

(12) United States Patent
Sohlden et al.

(10) Patent No.: US 10,716,627 B2
(45) Date of Patent: Jul. 21, 2020

(54) METHOD AND SYSTEM FOR PLANNING A SURGICAL INSTRUMENT PATH

(71) Applicant: COVIDIEN LP, Mansfield, MA (US)

(72) Inventors: Ryan Sohlden, Lyons, CO (US); Sharif Razzaque, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 302 days.

(21) Appl. No.: 15/585,649

(22) Filed: May 3, 2017

(65) Prior Publication Data
US 2018/0318009 A1 Nov. 8, 2018

(51) Int. Cl.
| A61B 34/10 | (2016.01) |
| A61B 90/96 | (2016.01) |
| A61B 90/98 | (2016.01) |
| A61B 6/03 | (2006.01) |
| A61B 90/00 | (2016.01) |

(Continued)

(52) U.S. Cl.
CPC .............. *A61B 34/10* (2016.02); *A61B 90/96* (2016.02); *A61B 90/98* (2016.02); *A61B 6/032* (2013.01); *A61B 2034/102* (2016.02); *A61B 2034/105* (2016.02); *A61B 2034/107* (2016.02); *A61B 2034/2065* (2016.02);
(Continued)

(58) Field of Classification Search
CPC ......... A61B 34/10; A61B 90/96; A61B 90/98; A61B 2034/102; A61B 2034/107; A61B 2034/2065; A61B 2090/061; A61B 2090/3762; A61B 6/032; A61B 2562/221; G06T 11/60
See application file for complete search history.

(56) References Cited

U.S. PATENT DOCUMENTS

| 6,086,544 A | 7/2000 | Hibner et al. |
| 7,014,633 B2 | 3/2006 | Cragg |

(Continued)

FOREIGN PATENT DOCUMENTS

| KR | 10-2017-0030690 A | 3/2017 |
| WO | 2015135057 A1 | 9/2015 |

OTHER PUBLICATIONS

Figueira, C. et al., Medical Staff extremity dosimetry in CT fluoroscopy: an anthropomorphic hand voxel phantom study. Physics in Medicine and Biology, vol. 58, 2013. p. 5433-5448 (Year: 2013).*

(Continued)

*Primary Examiner* — Theodore J Stigell
*Assistant Examiner* — Sean A Frith

(57) ABSTRACT

A method of planning path for a surgical instrument is provided for use during a surgical procedure. The method includes identifying a treatment target in images of a patient to be treated during a surgical procedure, determining dimensions of the patient, a surgical instrument, and an external obstruction, and determining a path to guide the surgical instrument to the treatment target during the surgical procedure. The surgical instrument is configured to be used during the surgical procedure. The external obstruction is an object external to the patient's body that interferes with one or more potential paths of the surgical instrument. The path is determined such that the surgical instrument avoids the external obstruction based on the determined dimensions of the surgical instrument and the determined dimensions of the external obstruction.

20 Claims, 6 Drawing Sheets

(51) Int. Cl.
*A61B 34/20* (2016.01)
*G06T 11/60* (2006.01)

(52) U.S. Cl.
CPC . *A61B 2090/061* (2016.02); *A61B 2090/3762* (2016.02); *A61B 2562/221* (2013.01); *G06T 11/60* (2013.01)

(56) References Cited

U.S. PATENT DOCUMENTS

| | | | |
|---|---|---|---|
| 7,510,534 B2 | 3/2009 | Burdorff et al. | |
| 7,835,784 B2 | 11/2010 | Mire et al. | |
| 7,840,253 B2 | 11/2010 | Tremblay et al. | |
| 9,504,530 B2 | 11/2016 | Hartmann et al. | |
| 2001/0019599 A1* | 9/2001 | Guendel | A61B 6/032 378/15 |
| 2014/0270441 A1 | 9/2014 | Baker | |
| 2014/0276943 A1* | 9/2014 | Bowling | A61B 17/16 606/130 |
| 2014/0330108 A1 | 11/2014 | Dempsey | |
| 2015/0057526 A1* | 2/2015 | Gerken | A61B 6/54 600/411 |
| 2015/0201892 A1 | 7/2015 | Hummel et al. | |
| 2016/0302871 A1* | 10/2016 | Gregerson | A61B 34/20 |
| 2017/0304020 A1* | 10/2017 | Ng | A61B 34/20 |

OTHER PUBLICATIONS

International Search Report issued in corresponding Appl. No. PCT/US2018/030655, dated Aug. 29, 2018 (6 pages).
International Preliminary Report on Patentability issued in corresponding Int'l Appl. No. PCT/US2018/030655 dated Nov. 5, 2019 (5 pages).

\* cited by examiner

METHOD AND SYSTEM FOR PLANNING A SURGICAL INSTRUMENT PATH

BACKGROUND

1. Technical Field

The present disclosure relates generally to systems and methods for planning a path to navigate a surgical instrument, such as an ablation needle, to a target treatment site. Specifically, the present disclosure relates to planning an entry point and a trajectory for positioning a surgical instrument through a patient's tissue that avoids critical structures and which provides sufficient clearance enabling maneuverability of the surgical instrument while the patient is within the bore of a CT scanner.

2. Background of Related Art

In the treatment of diseases such as cancer, procedures are often performed wherein elevated or reduced temperatures are applied to tumors to kill the cancer cells. In one such procedure, needle-ablation, a needle-like device is placed within a treatment target, such as a tumor, inside of a patient. Once the needle-like device is within the treatment target, a heating or cooling element is supplied to the needle to heat or cool the target, or alternatively, the needle-like device may output electromagnetic radiation to heat diseased cells to temperatures above 41° C.

The typical needle-ablation procedure proceeds as follows. A patient initially undergoes a diagnostic pre-operative CT or MRI scan days or weeks before the needle-ablation procedure is to be performed in order to generate pre-operative images of the patient. Using the pre-operative images, a clinician may identify and locate a treatment target. Once the treatment target is identified, the clinician may then, optionally, devise an initial plan for an entry position for the needle on the patient's skin and a trajectory for the needle to proceed through the patient's tissue to the treatment target while avoiding critical structures, such as organs (e.g. gall bladder or heart) and large vessels, and obstructions (i.e. bones). Typically, because the CT scan produces images that show slices of the patient, clinicians will typically devise a trajectory within a single 2D axial plane of the body so as to work within a single image and simplify the process of planning the trajectory. However, by generating a plan within a single 2D axial plane of the body, or single slice of the CT scans, the clinician in considerably limited in the number of possible trajectory plans.

Once the initial plan is established, the patient is positioned lying on the table of a CT scanner so that the patient may be moved into and out of a bore of the CT scanner in order to take intraoperative CT images of the patient during the procedure. The patient is moved into the bore of the CT scanner and undergoes a first intraoperative CT imaging to generate images, with which, the clinician may revise, or devise for the first time if not previously done, a plan to guide the needle to the treatment site, including an entry position and a trajectory. After the first intraoperative CT imaging scan is complete, the patient is removed from the bore of the CT scanner, the clinician inserts the needle into the patient and advances the needle a short distance through the patient's tissue. The clinician attempts to insert the needle at the planned entry position and to follow the planned trajectory, but cannot be certain of the placement of the needle. In order to determine whether the needle has been placed accurately, the patient is moved back within the bore of the CT scanner and the patient is imaged with the needle partially positioned into the patient.

After the second scan is complete, the patient is once again removed from the bore of the CT scanner. If the clinician determines that the needle enters the patient at the wrong entry position or that the needle is following the wrong trajectory, the clinician removes the needle and attempts to relocate the needle to the correct entry position and to follow the correct trajectory. Once the needle is re-placed, the patient is moved back into the bore of the CT scanner for another intraoperative scan. Placing the needle at a new entry position and/or trajectory and performing intraoperative scans repeats until the scans indicate that the needle enters the patient at the planned entry position and is directed along the planned trajectory to the target. Once the needle enters the patient at the planned entry position and is directed along the planned trajectory to the target, the clinician progresses the needle further into the patient. With each incremental progression of the needle, an additional intraoperative scan is performed on the patient. If the needle has strayed from the planned trajectory, the clinician, after removing the patient from the bore of the CT scanner, adjusts the needle angle as needed before reimaging the patient to determine if the adjustment has corrected the approach to the treatment target. Once the treatment target is reached the procedure may be performed.

This typical needle-ablation procedure, as described above, requires the clinician to continually guess as to the entry position and trajectory of the needle and requires the patient be continually moved into and out of the bore of the CT scanner in order to check the clinician's guess as to the placement and progression of the needle, since it is difficult for the clinician to manipulate the needle with the patient positioned within bore of the CT scanner. The entire process can be considerably time consuming and tiring for the clinician and may require the needle be inserted into the patient multiple times. In addition, the plan for the needle trajectory toward the target does not take into account the location of the bore of the CT scanner, and as a result, when the patient is moved back within the bore of CT scanner to be imaged, the bore may interfere with the needle. In such cases where the bore interferes with a portion of the positioned needle, the needle would need to be removed and a new plan for the entry position and trajectory of the needle would need to be devised. Finally, in the existing needle-ablation procedure, the devised trajectory of the needle may require the needle to reach a target for which the needle shaft of the needle is too short (the handle must remain outside the patient).

SUMMARY

Provided in accordance with the present disclosure is a method of planning a path for a surgical instrument for use during a surgical procedure. The method includes identifying a treatment target within images of a patient to be treated during a surgical procedure, determining dimensions of a patient, determining dimensions of a surgical instrument configured to be used during the surgical procedure, determining a location of the external obstruction relative to the patient, and planning an instrument path for guiding the surgical instrument to the treatment target during the surgical procedure. The instrument path is determined such that the surgical instrument avoids the external obstruction based on the determined dimensions of the surgical instrument and the determined dimensions of the external obstruction.

In an aspect of the present disclosure, the method further includes scanning the patient with at least one of a CT scanner or an MRI scanner to generate the images of the patient.

In another aspect of the present disclosure, the external obstruction is a CT scanner.

According to yet another aspect of the present disclosure, determining dimensions of the surgical instrument includes determining dimensions of cables coupled to the surgical instrument.

According to an additional aspect of the present disclosure, the method further includes determining dimensions of a clinician's hand. The instrument path is further planned such that the clinician's hand may manipulate the surgical instrument while avoiding the external obstruction during the surgical procedure In an aspect of the present disclosure, the method further includes performing dosimetry simulation for the clinician's hand along planned instrument path and displaying results of the dosimetry simulation.

In another aspect of the present disclosure, determining dimensions of a clinician's hand includes at least one of receiving a user entered glove size, receiving user entered hand dimensions, or imaging the clinician's hand.

According to yet another aspect of the present disclosure, the method further includes generating a model of the patient from the images of the patient and displaying the model of the patient on a display.

According to an additional aspect of the present disclosure, the method further includes displaying the instrument path on the display superimposed in the model of the patient.

In an aspect of the present disclosure, the method further includes imaging the patient during the procedure with surgical instrument inserted into the patient and displaying a location of the surgical instrument on the display superimposed over the model of the patient and the displayed instrument path.

In another aspect of the present disclosure, the method further includes generating a model of the external obstruction from the dimensions of the external obstruction and displaying the model of the external obstruction on the display at the location of the external obstruction relative to the patient.

According to yet another aspect of the present disclosure, the method further includes generating a model of the surgical instrument from the dimensions of the surgical instrument and displaying the model of the surgical instrument on the display.

According to an additional aspect of the present disclosure, the method further includes receiving a user input instructing a change in at least one of a location or an orientation of the model of the surgical instrument and displaying a projected path from the model of the surgical instrument according to the location and the orientation of the displayed model of the surgical instrument.

In an aspect of the present disclosure, the method further includes receiving a user input accepting the location or the orientation of the model of the surgical instrument. The instrument path is further planned according to the location and the orientation of the model of the surgical instrument accepted by the user.

According to an additional aspect of the present disclosure, the method further includes displaying the model of the surgical instrument on the display according to the user input instructing a change in at least one of the location or the orientation of the model of the surgical instrument, if planning the instrument path for the surgical instrument to the treatment target during the surgical procedure such that the surgical instrument avoids the external obstruction can be performed according to the user instructed location and orientation of the model of the surgical instrument.

In another aspect of the present disclosure, the method further includes displaying the model of the surgical instrument on the display according to the user input instructing a change in at least one of the location or the orientation of the model of the surgical instrument.

According to yet another aspect of the present disclosure, the method further includes generating a warning if planning the instrument path to guide the surgical instrument to the treatment target during the surgical procedure such that the surgical instrument avoids the external obstruction cannot be performed according to the user instructed location and orientation of the model of the surgical instrument.

According to an additional aspect of the present disclosure, the method further includes modifying the user instructed location and orientation of the model, if planning the instrument path to guide the surgical instrument to the treatment target during the surgical procedure such that the surgical instrument avoids the external obstruction cannot be performed according to the user instructed location and orientation of the model of the surgical instrument.

According to an additional aspect of the present disclosure, the method further includes determining whether the shaft can reach the treatment target while the handle remains outside of the patient.

In an aspect of the present disclosure, determining dimensions of the surgical instrument includes reading one of a coded resistor, data stored on a ROM, a bar code, or an RFID tag associated with the surgical instrument.

Further, to the extent consistent, any of the aspects described herein may be used in conjunction with any or all of the other aspects described herein.

BRIEF DESCRIPTION OF THE DRAWINGS

Embodiments of the present disclosure are described herein with reference to the accompanying drawings, wherein.

DETAILED DESCRIPTION

As will be described in detail below, provided is a planning system and methods for planning a path for a surgical instrument to follow during a surgical procedure. Specifically, the system and methods provide for planning a path for a surgical instrument to follow such that the surgical instrument may be properly utilized and positioned without interference with an obstruction external to patient "P".

Predominantly, the obstruction is described herein as a CT scanner. However, it should be understood that the planning system and methods described herein may be utilized with various obstructions that may be present during the performance of various surgical procedures. Those obstructions include, but are not limited to, for example, MRI scanner, a PET scanner, a cone-beam CT scanner, a collimated CT scanner, a C-arm fluoroscopic imager, a surgical CT scanner, a surgical MRI scanner, or a robotically positioned imaging emitter or detector.

Figure 1:
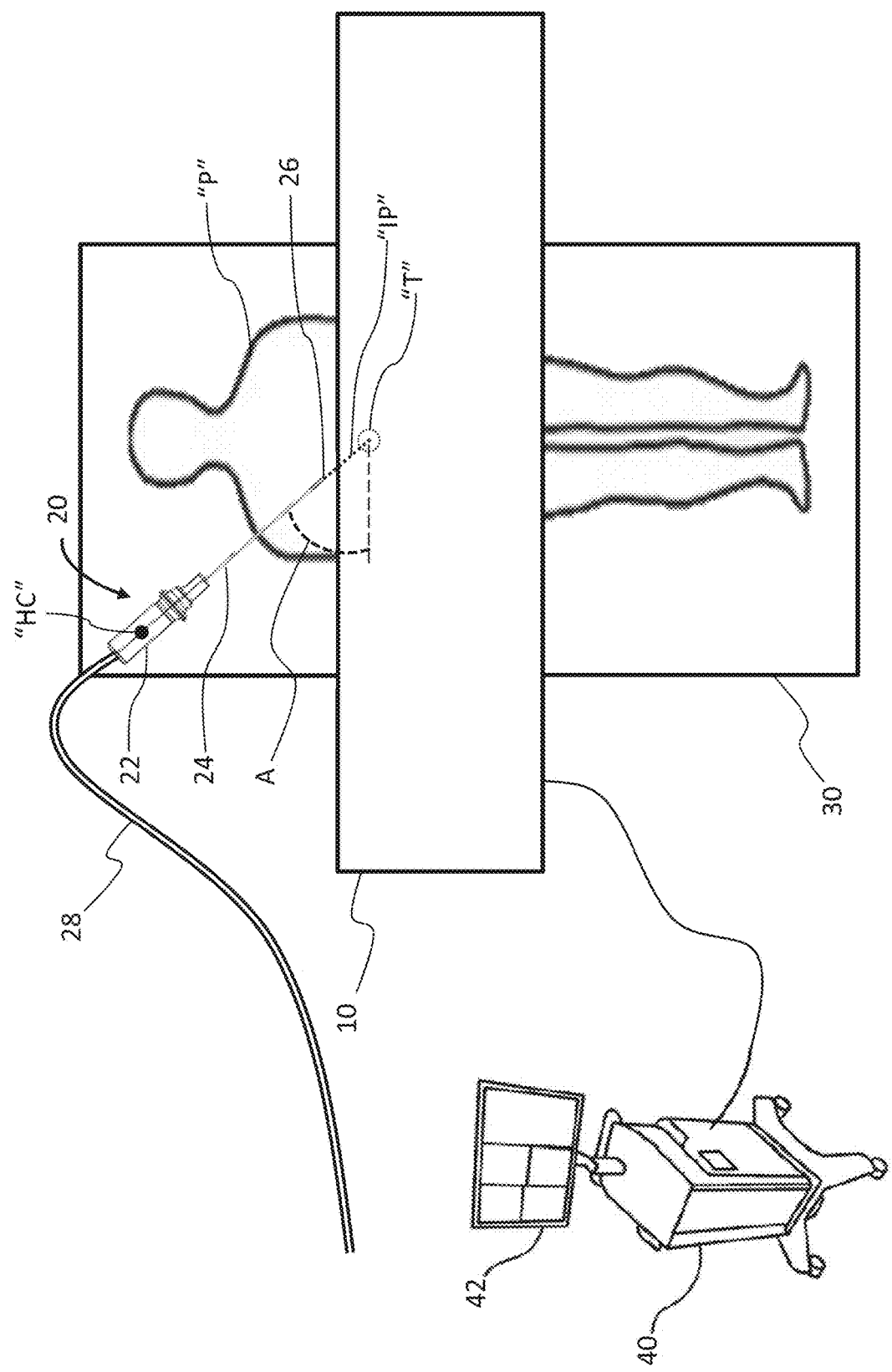
FIG. 1 is a schematic illustration of a patient within a CT scanner in accordance with the present disclosure.

Referring initially to FIG. 1, there is shown schematic illustration of an elevated view of a CT scanner 10 with a patient "P" within CT scanner 10. Patient "P" is positioned on a table 30 and is shown within a CT bore 18 (see FIG. 2) of CT scanner 10. Table 30 allows patient "P" to be moved into and out of the bore of CT scanner 10 in order to image a portion of patient "P". FIG. 1 also includes surgical instrument 20, shown directed toward target "T" with an instrument path "IP" projected therefrom at an angle "A" with respect to a horizontal axis through the target "T" and parallel to an edge of CT scanner 10.

Surgical instrument 20 is shown including a handle 22, a shaft 24, a distal portion 26, and cable 28. Handle 22 is shown including a point representing handle center "HC" about which a clinician would grip handle 22. While shown including handle 22, it is contemplated herein the surgical instrument 20 may not include a handle and may instead be controlled, for example, using a robotic arm. Cable 28 is shown extending from a proximal end of surgical instrument 20. Cable 28 allows surgical instrument 20 to be connected to, for example, an electrosurgical or microwave generator (not shown), a source of heat or chilled fluid (not shown), a vacuum device (not shown), workstation 40, or other devices associated with surgical procedures commonly performed.

Surgical instrument 20 may be any device configured to puncture patient's "P" skin and either treat or take a sample from target "T" or provide access through the tissue so that another treatment device may be guided through surgical instrument 20 to treat or take a sample from target "T". Accordingly, surgical instrument 20 may be, for example, an ablation device (e.g. microwave probe, cryoablation probe, radiofrequency probe), a trocar, a tube or cannulae, a probe, a biopsy needle, an electrocautery device, a temperature sensor, a suction device, electroporation probes, an injection needle, an optical coherence tomography probe, an endoscopic camera, a spinal fixation needle, an in-vitro fertilization device, a catheter, etc. Treatment target "T" may therefore be, for example, a cancerous tumor, an identified mass, an internal cut or wound, an organ, a membrane, or any other medically significant bodily structure requiring attention, treatment, or measurement.

Surgical instrument 20 is shown directed toward target "T" with instrument path "IP" extending from a position external the patient "P" to the target "T". Instrument path "IP" is shown directed toward target "T". However, while directing instrument path "IP" toward target "T" is an objective of the current disclosure, instrument path "IP" may not be directed toward target "T" during portions of the planning procedure. Angle "A" describes an angle between surgical instrument 20 and a line, parallel to the edge of CT scanner 10, running through target "T".

FIG. 1 further includes workstation 40. Workstation 40 includes software and/or hardware used to facilitate pathway planning, performing geometrical analysis, compiling CT or other types of images into geometric models, and performing general calculations. Workstation 40 includes application 42 which may perform these functions, and more particularly, the functions described with more detail below with reference to FIGS. 3-5.

Figure 2:
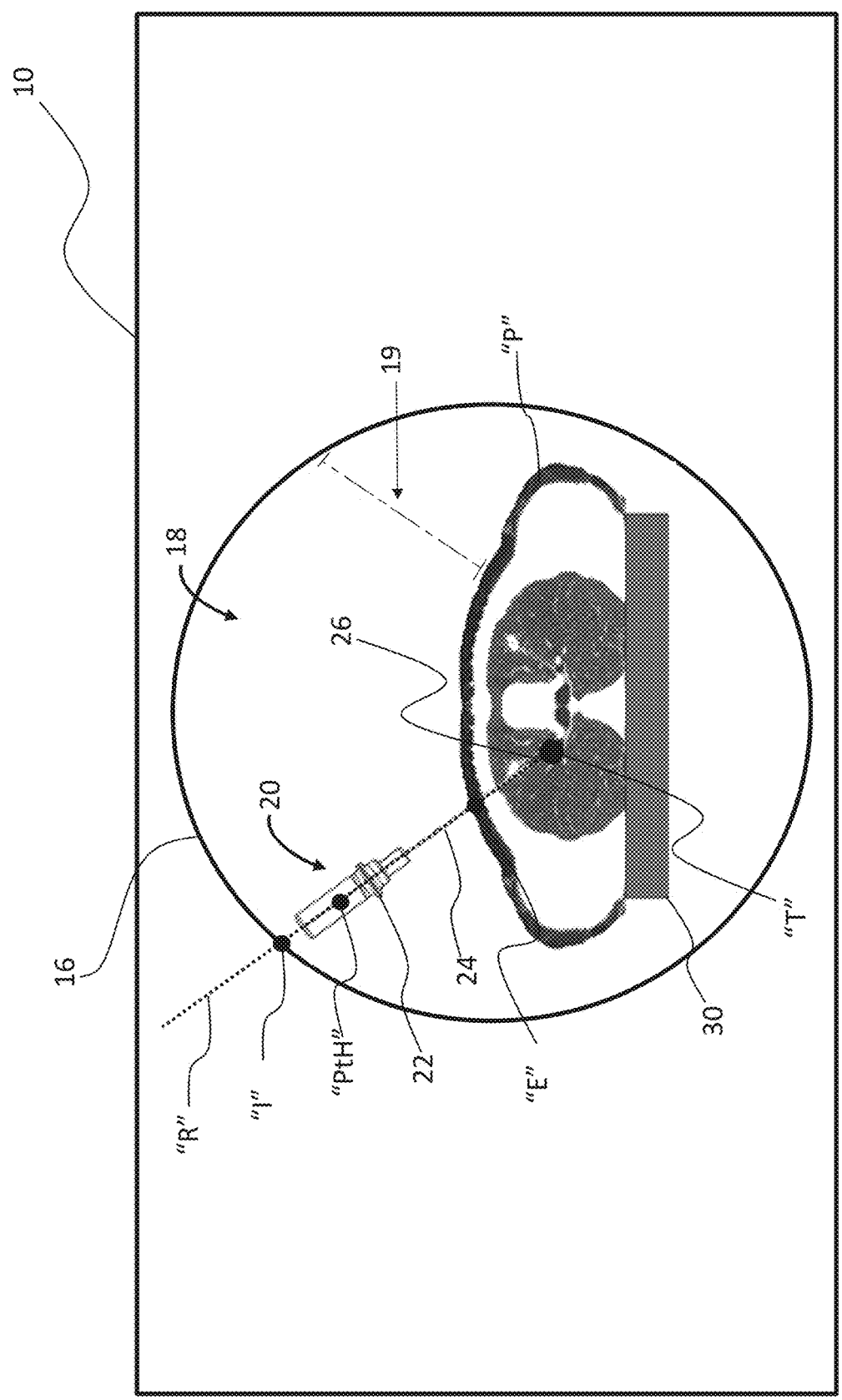
FIG. 2 is a perspective view of a patient within a CT scanner in accordance with the present disclosure.

Turning now to FIG. 2, there is shown a front view of patient "P" positioned within CT bore 18 of a CT scanner 10 in accordance with the present disclosure. CT bore 18 is an empty space within CT scanner 10 defined by a CT bore surface 16. FIG. 2 also represents an exemplary display that may be shown on display 606 (See FIG. 6) of workstation 40. FIG. 2 shows trajectory "R" projecting from target "T" through entry point "E", the point at which instrument 20 will puncture and enter patient's "P" tissue, and through bore intersection "I", which represents the location of a potential intersection of surgical instrument 20 and CT bore surface 16. Because surgical instrument 20 is designed to extend through patient's "P" skin to reach target "T", the length dimension of surgical instrument 20 is typically the most significant dimension in determining whether surgical instrument's 20 path will be obstructed by an obstruction, for example, CT bore surface 16. Therefore, bore intersection "I" represents a significant location for determining whether surgical instrument's 20 path will be obstructed by an obstruction, for example CT bore surface 16.

In determining a path to target "T," internal obstructions, such as bones, organs, and other critical structures may impede surgical instrument's 20 path to the target. In addition, external obstructions, such as CT scanner 10 may also impede surgical instrument's 20 path to the target. Therefore, the present disclosure is directed toward a system and method for developing a path to target "T" while allowing a clinician to maneuver surgical instrument 20 in CT bore 18 without colliding with CT bore surface 16 along trajectory "R" which projects from the treatment target through bore intersection "I."

Figure 3:
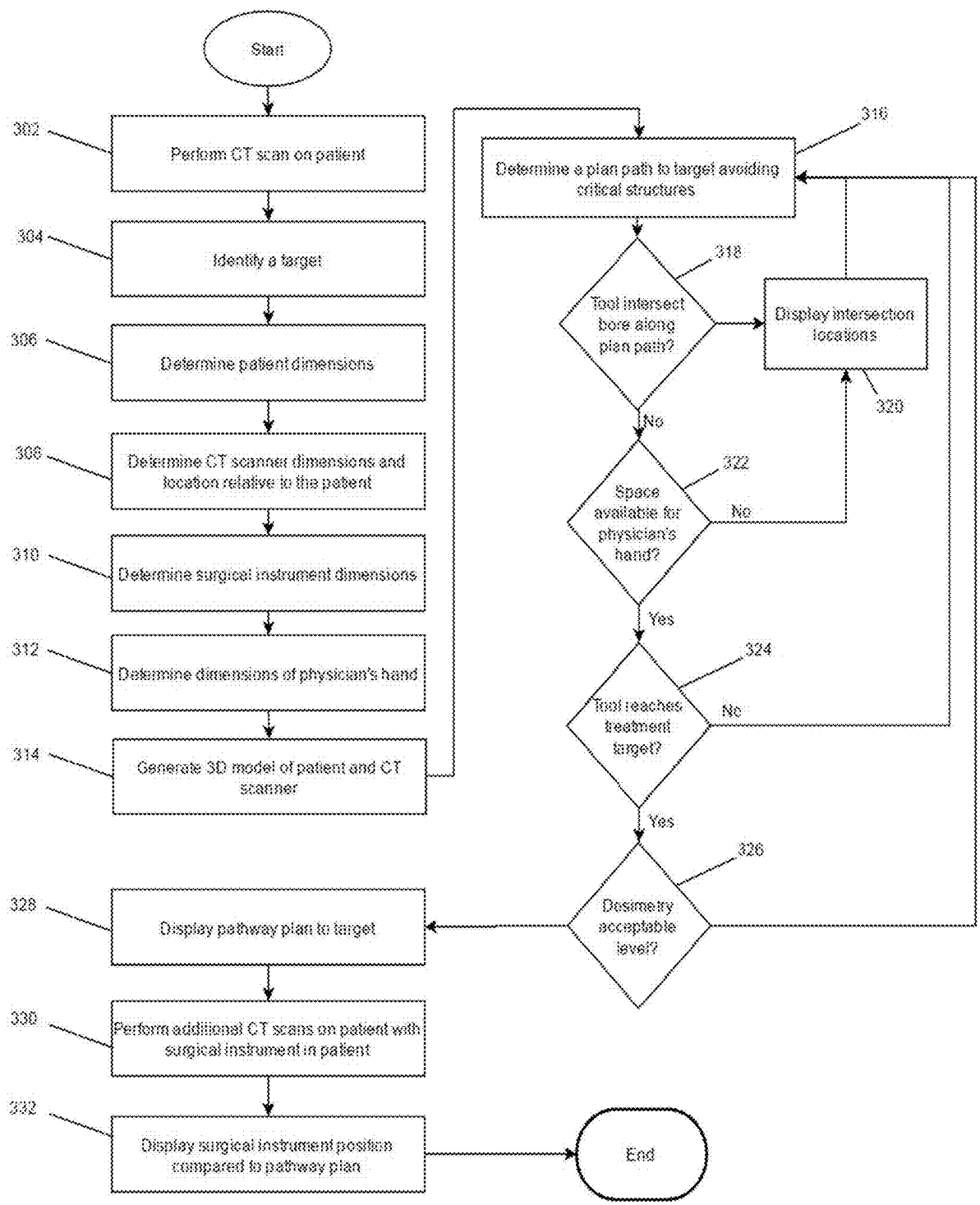
FIG. 3 is a flowchart illustrating a process of planning a path for a surgical instrument according to embodiments of the present disclosure.
Figure 4:
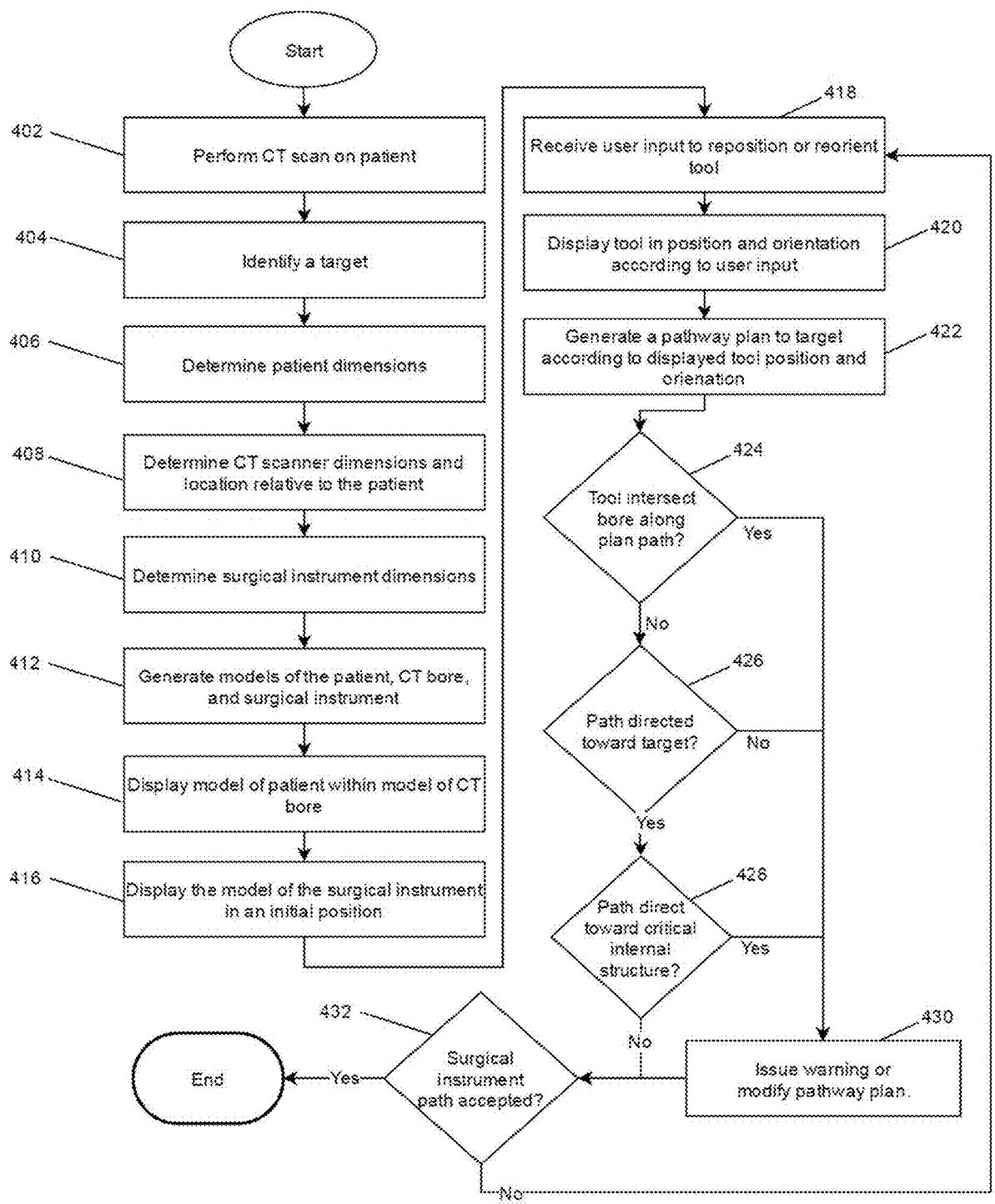
FIG. 4 is a flowchart illustrating another process of planning an entry a path for a surgical instrument according to embodiments of the present disclosure.
Figure 5:
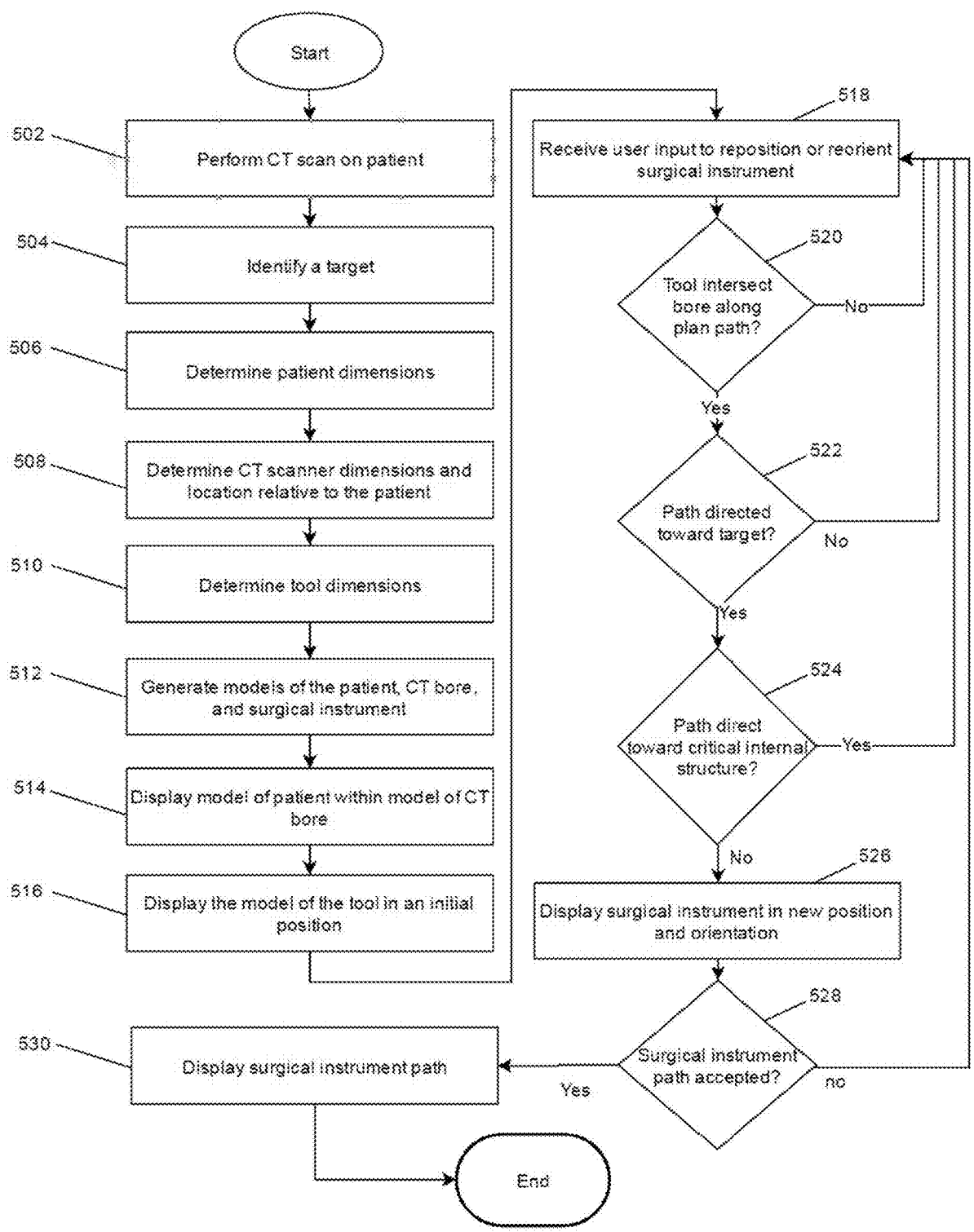
FIG. 5 is a flowchart illustrating an additional process of planning an entry point and trajectory of a surgical instrument according to embodiments of the present disclosure.
Figure 6:
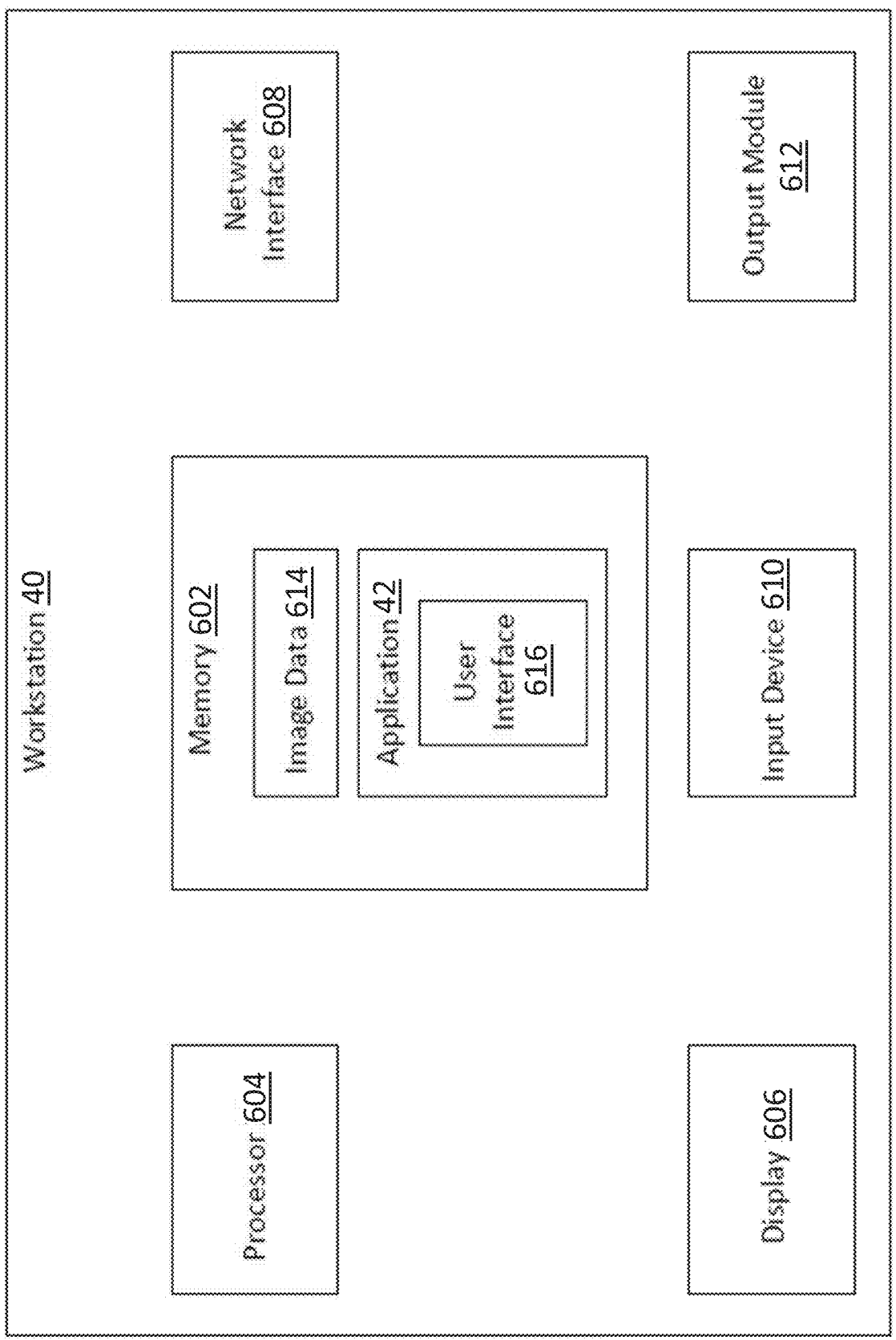
FIG. 6 is a schematic block diagram of a workstation configured for use with the system of FIG. 1.

Referring now to FIGS. 3-5, flowcharts are shown illustrating processes of planning a path to target "T" for a surgical instrument according to embodiments of the present disclosure. The processes may be implemented, at least in part, by workstation 40 and by application 42. In performing the processes, processor 604 executes instructions stored in the memory 602 (FIG. 6). The particular sequence of steps shown in FIGS. 3-5 may be executed in sequences other than the sequence shown in FIGS. 3-5 without departing from the scope of the present disclosure. Further, some steps shown in processes of FIGS. 3-5 may be concurrently executed with respect to one another instead of sequentially executed with respect to one another. Moreover, the steps shown in each of FIGS. 3-5 may be integrated into, and executed as part of, the other processes of FIGS. 3-5. The processes of FIGS. 3-5 are described with reference to FIGS. 1 and 2.

The process of FIG. 3 begins at step S302. At step S302, an area of interest, for instance the chest and lungs, of a patient is imaged using imaging methods such as, for example, a CT scan or an MRI scan. At step S304, a target "T", such a cancerous growth, is identified in the images generated in step S302. A clinician may identify the target or the target may be determined by workstation 40 or other computer systems using image analysis software.

During steps S306-S312, as will be further described below, various dimensions are determined in order to: 1) determine physical limitations which limit the paths of surgical instrument 20 to follow to approach the target; and 2) develop models of those elements that limit the paths of surgical instrument 20.

At step S306, a patient's dimensions are determined. Generally, the initial images of patient "P", generated at step S302, provide workstation 40 with sufficient information to determine patient's "P" dimensions. However, subsequent scans may be performed to determine patient's "P" dimensions. Application 42 performs image processing and analysis on the images generated by CT scanner 10 to determine patient dimensions and a location of patient "P" within the image. The performance of image processing may include, for example, establishing a threshold limit for individual voxels to distinguish between air (characterized by dark black shading) surrounding the patient and patient tissue (characterized by lighter shading) which is given by the radiodensity of the matter being imaged. If an individual voxel exceeds a Hounsfield value, the voxel is judged to be a voxel showing a portion of tissue, and if an individual voxel does not exceed the Hounsfield value, the voxel is judged to be a voxel showing air. From there, workstation 40 may determine an edge of patient's "P" tissue by determining which tissue voxels are located proximate air voxels and drawing an outline of the patient "P" according to adjacent tissue voxels that are located proximate air voxels along a line. Alternatively, workstation 40 may determine which tissue voxels are furthest from a point within patient's "P" expected position or from a point determined according to weighted average voxel location determined by voxel values and their locations in order to determine that such voxels are tissue edge voxels. Once an edge between patient "P" and the air is determined, workstation 40 may measure the dimensions of the outline and generate a geometric solid model of patient's "P" tissue.

Patient's "P" measurements may also be determined by physically measuring patient "P" and entering the measurements into workstation 40 using input device 610. Workstation 40 may also connect to a network and download patient measurements from a patient file on a connected network. It is also contemplated that, as described further below at step S308, the dimensions of patient "P" may be determined at the same time dimensions of CT scanner 10 are determined and further may be determined only in relation to CT scanner 10. In some embodiments of the present disclosure, the dimensions of patient "P" need not be determined. Instead, the process may operate by determining a clearance 19. Clearance 19 is defined as a space between patient "P" and CT bore surface 16. Clearance 19 represents a space, above patient "P," in which the clinician may occupy or surgical instrument 20 may occupy without interference from CT bore surface 16. Similar to the process described above, edge voxels of patient "P" are determined, but specific measurements of patient "P" need not be determined from those voxels. Instead, only an area or volume of the darker air voxels, representing clearance 19, is determined and measured to assess what space surgical instrument 20 may occupying and travel through as surgical instrument 20 approaches target "T."

At step S308, dimensions of example obstruction, CT scanner 10, which is defined by CT bore surface 16, and a location of the CT bore surface 16 are determined relative to patient "P". When performing CT imaging, CT scanner 10 images the air within CT bore 18. Similar to the process described above with respect to patient "P", voxel threshold analysis may be used to determine which voxels are air voxels and which voxels represent CT bore surface 16. CT scanner 10, as a solid object, will generate lighter voxels than the surrounding air, and thus, workstation 40 may discern between CT scanner voxels and air voxels to determine a location and dimension of CT scanner 10 bore 16. Stated differently, workstation 40 segments the CT images with a threshold to identify the air in the bore-clearance 18. If the CT images are noisy, workstation 40 may apply a statistical fit (using, for example, a least-squares fit or other appropriate methods using computational geometry) to segment the air to a cylindrical model.

Just as the specific dimensions of patient "P" need not be determined, as described above, the dimensions of CT bore surface 16 need not be determined. Instead, workstation 40 may determine only which voxels are air voxels and may measure an area or volume of air voxels to determine a clearance, or available space for the clinician to work, for instrument 20 to be manipulated, or for surgical instrument 20 to occupy, between patient "P" and CT scanner 10, without specifically determining the dimensions of either patient "P" or CT scanner 10. Additionally, where the CT images are noisy, the system may statistically fit (using least-squares or other appropriate methods familiar to those skilled in the art of computational geometry) the segmented air to a cylindrical model.

In the alternative, CT bore surface 16 dimensions and position may be determined according to a look-up table of values defining a bore size and position according to a specific brand name and model number of CT scanner 10. Moreover, CT bore surface 16 dimensions and position may be written on human-readable label or may be encoded in a machine readable label, such as a barcode or an RFID. CT scanner 10 may also be imaged by a 3D scanning device. Possible 3D scanning devices include, but are not limited to, a hand-held laser scanner, a structured light scanner, a modulated light scanner, a stereoscopic scanner, a photometric scanner, and a silhouette scanner. Example commercial scanners that may be used include Microsoft Kinect™ camera, Intel Realsense™ camera, and PrimeSense™ camera.

At step S310, dimensions of surgical instrument 20 are determined. In some embodiments, workstation 40 includes computational models (e.g. a CAD model) of various types and sizes of surgical instruments, from which a user may select surgical instrument 20. Alternatively, workstation 40 may automatically identify surgical instrument 20 when it is connected to workstation 40 (via a coded resistor, data stored on a ROM in the surgical instrument, bar code, RFID, etc.).

At step S312, dimensions of the clinician's hand are determined. The clinician's hand may be physically measured and the clinician enters those dimensions into workstation 40 using input device 610. Alternatively, if the clinician knows his or her hand size, the clinician may enter a glove size, and, based on look-up tables describing hand dimensions according to glove size, workstation 40 may determine the dimensions of the clinician's hand. The clinicians hand may also be scanned using a 3D scanner commonly known in the art (e.g. Microsoft Kinect™ camera, Intel Realsense™ camera, PrimeSense™ camera). The 3D scanner may be used separate of the system and the dimensions may be entered into workstation 40 using input device 610, or the 3D scanner may connect directly to workstation 40. Additionally, dimensions of the clinician's specific hand may not be necessary. If an approximation of the clinician's hand is sufficient, workstation 40 may use average or "one-size-fits all" hand measurements based on stored hand measurements or hand measurements obtained from a server.

At step S314, a 3D model of patient "P" within the CT bore 18 is generated by workstation 40 to established locations within a 3D space according to dimensions and locations determined in steps S306 and S308. Patient "P" may be modeled using techniques commonly known within the art to combine the CT scans and generate a 3D model of patient "P". Similarly, a geometric model of CT bore surface 16 may be generated at a location given by measurements determined in step S308.

Models of surgical instrument 20 and the clinician's hand may also be generated. However, models of the surgical instrument 20 and the clinician's hand are not necessary as they may be characterized merely by their dimensions, and those dimensions may compared to dimensions determined from the 3D model of patient "P" and CT scanner bore 16 as described further with respect to steps S318 and S320.

At step S316, a path plan is prepared for guiding surgical instrument 20 to the target using the CT images. The clinician or workstation 40 determines locations of critical structures, including organs (e.g. gall bladder or heart) and large vessels, and obstructions (i.e. bones), and determines entry point "E" and trajectory "R" through a patient's tissue to the target that avoids critical structures. The path is then input into workstation 40 using user interface 616. The path may also be developed using workstation 40. The entry point "E" may be received as an input coordinate position, and workstation 40 may determine the trajectory by establishing a straight line between target "T" and entry point "E". Alternatively, the clinician may input an angle "A" with respect to target "T" in order to project trajectory "R" projecting from target "T" at angle "A". Furthermore, as will be further described with respect to FIGS. 4 and 5, the clinician may manipulate a model of surgical instrument 20 on a display of the 3D model of patient "P" and CT scanner 10 generated in step S314 and input position and orientation of the surgical instrument 20 according to the manipulated location of the surgical instrument 20.

Once a path plan is determined, at step S318, workstation 40 computes whether any part of surgical instrument 20 will intersect with the CT bore surface 16 during the procedure using a 3D model of surgical instrument 20. A 3D model of surgical instrument 20, based on the determined measurements of surgical instrument 20, is superimposed on the 3D model of patient "P" and CT bore surface 16 generated at step S314 according to inputs received at workstation 40 using user interface 616. Application 42 performs geometric subtracting (e.g. geometric Boolean subtraction) to determine measurements of CT bore 18 as defined by CT bore surface 16. Then, workstation 40 determines whether the model of surgical instrument 20 will intersect CT bore surface 16 using the length of surgical instrument 20, target "T," and entry point "E". Alternatively, workstation 40 may determine whether the model of surgical instrument 20 remains within bore clearance 19 while surgical instrument is entirely outside of the patient.

As described in reference to FIG. 1, surgical instrument 20 may include cable 28. While cable 28 may be a rigid structure, it is often a flexible component that may be positioned in multiple orientations. Therefore, cable 28 may be modeled according to cable's 28 stiffness and maximum tolerable bending according to measurements determined regarding instrument 20 at step S310 or according to measurements recorded on an indicator (e.g. a coded resistor, data stored on a ROM of the surgical instrument, bar code, RFID, etc.) associated with surgical instrument 20. The modeling of cable 28 dictates various positions that cable 28 may be oriented. Therefore, workstation 40 positions cable 28 at various positions, according to the stiffness and maximum tolerable bending of cable 28, in order to determine whether CT bore surface 16 interferes with cable 28 at any position or all positions. If there is at least one position of cable 28 in which CT bore surface 16 does not interfere with cable 28, workstation 40 may determine that the selected path plan is acceptable. Alternatively, the clinician may choose an orientation for cable 28 and input it into workstation 40. Practical considerations, such as the position of a device that cable 28 connects to may dictate a position of cable 28.

Similar to cable 28, surgical instrument 20 may also be flexible. Thus, surgical instrument 20 may be modeled according to surgical instrument's 28 stiffness and maximum tolerable bending according to measurements determined regarding instrument 20 at step S310 or according to measurements recorded on an indicator (e.g. a coded resistor, data stored on a ROM of the surgical instrument, bar code, RFID, etc.) associated with surgical instrument 20. Bending of tool may be simulated using finite-element analysis of the needle-shaft and patient tissue to generate a model of surgical instrument 20. From there, workstation 40 may simulate several surgical instrument locations to determine viable path options and determine whether any possible path options allow surgical instrument 20 to be maneuvered to target "T" without interference from CT bore surface 16. Additionally, the clinician may choose an orientation for surgical instrument 20 and input it into workstation 40 to determine a specific path and allow workstation 40 to determine whether that path is a viable option. Practical considerations, such as the position of a device that surgical instrument 20 connects to, may dictate a position of surgical instrument 20.

Alternatively, at step S318, workstation 40 first determines a location of surgical instrument 20 along trajectory "R" when surgical instrument 20 first enters patient "P" at entry point "E" or, more specifically, whether the distal-most portion of surgical instrument 20 is minimally within the surface of patient's "P" tissue. At this position, surgical instrument 20 extends from Patent's "P" tissue at entry point "E" into CT bore 18 toward CT bore surface 16 at distance that is equal to the full length of surgical instrument 20. If surgical instrument 20 extends from entry point "E" to or beyond bore intersection "I", then the surgical instrument 20 would collide with CT bore surface 16 during the procedure. Accordingly, if surgical instrument 20 will intersect with the CT bore during the procedure according to the planned pathway including entry point "E" and trajectory "R," the process proceeds to step S320 before returning to step S314 for the clinician to plan a new path plan. If surgical instrument 20 will not intersect with the CT bore during the procedure, the process proceeds to step S322.

In order to determine a length between entry point "E" and bore intersection "I", bore intersection "I" must first be determined. Using the 3D model generated at step S314, workstation 40 projects a ray along trajectory "R", through entry point "E", to bore intersection "I". Locations along trajectory "R" may be easily calculated according to the angle "A" and the location of target "T". From there, 3D coordinate locations along trajectory "R" may be compared to 3D coordinates established for CT bore surface 16. Once locations for entry point "E" and bore intersection "I" are established, a subtraction of the 3D coordinates gives the distance between them in each direction and subsequently a total distance can be determined.

At step S320, the 3D model of surgical instrument 20 is displayed superimposed on the 3D model of patient "P" and CT bore surface 16. Any portions of surgical instrument 20 that is determined, at step S318, to intersect with CT bore surface 16 is displayed indicating such an intersection. The display includes, for example, highlighted or colorized portions of the model of surgical instrument 20 that intersects CT bore surface 16. Additionally, any intersection points along CT bore surface 16 may be highlighted or colorized to further emphasize the point of contact.

At step S322, workstation 40 determines whether there is space available for the clinician's hand to manipulate surgical instrument 20. Using the clinician's hand dimensions, determined at step S312, workstation 40 models the clinician's hand placed on the 3D model of surgical instrument 20 within the 3D model of patient "P" and CT bore surface 16. The position and orientation of the hand are determined according to the type of surgical instrument 20 and its dimensions. Then, the clinician's hand may be considered to be a part of the 3D model of surgical instrument 20, such that, if either surgical instrument 20 or the clinician's hand intersects with CT bore surface 16 while distal portion 26 of surgical instrument 20 is positioned, the process returns to step S320 to display the intersections. If neither surgical instrument 20 nor the clinician's hand intersects CT bore surface 16, the process proceeds to step S324. Application 42 determines whether the clinician's hand fits within CT bore 18 while grasping surgical instrument 20 using the same method described above at step S318 with respect to surgical instrument 20.

The clinician hand may be modeled in a simplified manner as a sphere (or circle in 2D images) surrounding handle center "HC". Then, workstation 40 may utilize standard geometric collision software libraries, such as nVidia PhysX™, V-Collide, Unity3D™, Unreal Engine™, or using geometric collision algorithms, to determine whether the spherical model of the clinicians hand will intersect CT bore surface 16.

As an alternative method for determining whether the clinician's hand may appropriately manipulate surgical instrument 20 within CT bore 18, workstation 40 may determine a difference in the length of surgical instrument 20 and the distance between entry point "E" and bore intersection "I" in order to determine a distance between surgical instrument 20 and bore intersection "I" along which the clinician's hand may occupy. If the hand length exceeds the distance between surgical instrument 20 and bore intersection "I", workstation 40 determines that the CT bore surface 16 would interfere with the manipulation of surgical instrument 20. Moreover, if the distance between surgical instrument 20 and bore intersection "I" is within a certain threshold, workstation 40 may analyze dimensions of patient's "P" hand and of surgical instrument 20 in directions perpendicular to trajectory "R" to determine if surgical instrument 20 or the clinician's hand would intersect with CT bore surface 16 according to the curvature of CT bore surface 16 and the remaining length between surgical instrument 20 and bore intersection "I".

At step S324, workstation 40 determines whether, given the plan path, surgical instrument 20 will reach target "T". Distal portion 26 of surgical instrument 20 must reach target "T" in order to properly perform a procedure, such as an ablative treatment. Shaft 24 of surgical instrument 20 is designed to enter and travel through patient's "P" tissue. Handle 22 of surgical instrument 20 is designed to remain external to patient "P". Therefore, the length of shaft 24 must be great or equal to the distance between entry point "E" and target "T". Application 42 compares the length of shaft 24, determined as part of step S310, with the distance between entry point "E" and target "T". If the length of shaft 24 exceeds the distance between entry point "E" and target "T" the process proceeds to step S324. If the length of shaft 24 does not exceed the distance between entry point "E" and target "T" the process returns to step S316 for a new plan to be determined.

At step S324, workstation 40 performs a dosimetry simulation and a determination of whether the projected dosimetry is acceptable. During the procedure, the clinician may opt to perform continual imaging of the patient using continuous live imaging (for example, live fluoroscopy). If the clinician uses continuous live imaging to perform the procedure, the clinician's hand, located within CT bore 18 to manipulate surgical instrument 20, is subjected to the X-rays radiated and the clinician's hand will absorb a quantity of X-ray radiation. Because a clinician may commonly perform continuous live X-ray procedures and therefore may want to limit X-ray radiation exposure, workstation 40 may simulate a continuous live X-ray imaging procedure to determine how much radiation the clinician's hand, when located about handle 22 of surgical instrument 20, will absorb during the procedure. Application 42 calculates, according to the location of the clinician's hand, a length of the procedure, a strength of the X-ray radiation, and an absorption coefficient of human tissue, the dose of x-ray radiation the clinician's hand will absorb. Then, workstation 40 displays the calculated dosimetry on display 660 and the clinician may determine whether the displayed dosimetry is acceptable. Alternatively, workstation 40 may compare the calculated dosimetry to a preset dosimetry threshold to determine whether the dosimetry is acceptable. If the dosimetry is not acceptable, the process returns to step S316, allowing the clinician to determine a new instrument path "IP". If the dosimetry is acceptable, the process proceeds to step S328.

At step S328, the chosen path, having passed the tests described in steps S318-S322, is displayed along trajectory "R" on display 606 of workstation 40 superimposed upon the model of patient "P" and CT bore surface 16. The chosen path is shown as a colored or highlighted line connecting entry point "E" and target "T". The path may also be shown on a 2D projection of the 3D model of patient "P" and CT bore surface 16.

Once the treatment path is displayed, the clinician may commence the procedure. Patient "P" is placed on table 30 of CT scanner 10 and surgical instrument 20 is inserted into patient "P" a short distance. Then, at step S330, a CT scan is performed on patient "P" with the surgical instrument 20 partially inserted in patient "P". The CT images generated from the CT scan are displayed on display 606 along with the chosen path superimposed upon the model of patient "P" and CT bore surface 16. At step S332, the CT images and the path may be displayed side by side to allow the clinician to compare the actual location of surgical instrument 20 inside patient "P" and the planned location of surgical instrument. Also, the CT images of patient "P" with surgical instrument 20 inserted may be used to develop an intraoperative model of patient "P". The intraoperative model may be displayed side by side with the model of patient "P" and CT bore surface 16, or the intraoperative model may be displayed superimposed over the model of patient "P" and CT bore surface 16. Moreover, because the intraoperative CT images reflect more recent, up-to-date images, workstation 40 may compare various elements of the intraoperative images to the preoperative images used to develop the model of patient "P" and CT bore surface 16 and update the model of patient "P" and CT bore surface 16 according to any changes in position. The displayed path may likewise be updated according to the position or orientation of patient "P" in the intraoperative images.

If surgical instrument 20 is shown in the intraoperative CT images following the intended path, the clinician may advance surgical instrument 20 further into patient "P" before performing a subsequent intraoperative CT scan. If surgical instrument 20 is not shown to be following the intended path, the clinician withdraws surgical instrument 20 and repositions surgical instrument 20 before checking the new position with a subsequent CT scan. During this process, the clinician may manipulate surgical instrument 20 without removing patient "P" from CT bore surface 16. Once surgical instrument 20 reaches target "T", the path planning and navigation process is complete and the surgical procedure may be performed.

Turning to FIG. 4, there is shown another flowchart illustrating a process of planning a path for a surgical instrument consistent with embodiments of the present disclosure. Steps S402-S410 describe a process similar to that described by steps S302-S310 of FIG. 3. At step S412, workstation 40 generates a model of patient "P" and CT bore surface 16 and a model of surgical instrument 20. At step S414, the model of patient "P" and CT bore surface 16 is displayed on display 606. At step S416, the model of surgical instrument 20 is displayed superimposed upon the model of patient "P" and CT bore surface 16 at an initial position.

At step S418, user inputs are received by input device 610 instructing a change in position and orientation of the model of surgical instrument 20 from the initial position. The clinician, using for example, a touchscreen, a mouse, or other input device, may move and manipulate the orientation of the model of surgical instrument 20 by dragging the model of the surgical instrument around the model of patient "P" and CT bore surface 16 or by selecting a new locations for distal portion 26 of surgical instrument 20 (to determine entry point "E") and for a proximal portion of surgical instrument 20 (to determine angle "A"). Additionally, the clinician may input user inputs using, for example, a keyboard, to input 3D coordinates of entry point "E" and to input a value for angle "A". At step S420, the model of surgical instrument 20 is displayed superimposed upon the model of patient "P" and CT bore surface 16 at an initial position according to the orientation and position input by the clinician. At step S422, application generates instrument path "IP", a ray projecting from distal portion 26 of surgical instrument 20, and displays instrument path "IP" superimposed upon the model of patient "P" and CT bore surface 16. Instrument path "IP" may be emphasized with color or other means to accentuate instrument path "IP".

At step S424, workstation 40 determines whether CT bore surface 16 will interfere with surgical instrument 20 during performance of the procedure for the user input location and orientation of the model of surgical instrument 20. The process for determining whether CT bore surface 16 will interfere with surgical instrument 20 during performance of the procedure is described above in the description of step S318 of FIG. 3. If it is determined that CT bore surface 16 will interfere with surgical instrument 20, the process proceeds to step S430. If CT bore surface 16 will not interfere with surgical instrument 20, the process proceeds to step S426.

At step S426, workstation 40 determines whether instrument path "IP" is directed toward target "T". Application 42 describes instrument path "IP" according to an equation describing a ray starting at distal portion 26 and following a trajectory according to angle "A". Treatment target "T" is given by a 3D coordinate or by 3D coordinates describing a volume. If 3D coordinates of target "T" describe a point or location given by the equation for instrument path "IP", workstation 40 determines that instrument path "IP" is directed toward target "T". If instrument path "IP" is not directed toward target "T", the process proceeds to step S430. Otherwise, the process proceeds to step S428.

At step S428, workstation 40 determines whether instrument path "IP" intersects critical structures discernable on the CT scans. Application 42 performs image processing on the CT scans of patient "P", determining groups of adjacent voxels with similar voxel intensities. Application 42 then determines that groups of adjacent voxels represent locations of internal structure (e.g. bones, organs, or other structures discernable in the CT scan). After recognizing internal structures in the CT images, workstation 40 compares the size, location, CT intensity, and orientation of the internal structure, individually and relative to one another, to those of a patient model developed from scans of other patients. The comparison allows workstation 40 to determine the identity of structures identified in the CT scan and determine whether they are difficult to pass through, such as bones, or if the structures are critical to patient's "P" bodily function. If 3D coordinates of a structure deemed critical or difficult to penetrate describes a point location given by the equation for instrument path "IP", workstation 40 determines that instrument path "IP" is directed toward a critical structure. If instrument path "IP" is directed toward a critical structure the process proceeds to step S430. Otherwise, the process proceeds to step S432.

As described above, if at step S424, S426, or S428 workstation 40 determines that the path input by the clinician would be obstructed or would not reach the intended target "T", the process proceeds to step S430. At step S430, workstation 40 issues a warning indicating that the path input by the clinician is obstructed or is not directed to target "T". Additionally, at step S430, workstation 40 may determine a new entry point "E" proximate the entry point "E" input by the clinician and a new trajectory "R" that directs surgical instrument 20 toward target "T" from new entry point "E".

The warning may include displaying portions of CT bore surface 16 or patient "P" in color indicating points of interference. The warning may also include audio or text warnings describing the error or merely indicating the existence of some error. In some instances, the warning may only be dismissed and the process continued if patient "P" indicates a new entry point "E" and a new trajectory "R" that fits the criteria described in steps S424, S426, and S428.

At step S432, the clinician is prompted to select whether the input plan "P" is accepted and workstation 40 receives the user's input. If the clinician indicates that instrument path "IP" is not accepted, the process returns to step S418, allowing the clinician to choose a new instrument path "IP", and continually repeats steps S424-S432 until instrument path "IP" is accepted. Once the clinician indicates that instrument path "IP" is accepted, the planning process is complete and the clinician may then follow instrument path "IP" to reach target "T" without interference from CT bore surface 16 or critical structures within patient "P".

In FIG. 5, there is shown another flowchart illustrating a process of planning a path for a surgical instrument consistent with embodiments of the present disclosure. The planning process described in FIG. 5 is similar to the process described in FIG. 4. Steps S502-S518 describe a similar process as that described by steps S402-S318 of FIG. 4, and steps S520-524 describe a process similar to the process described by steps S424-S428 of FIG. 4. However, unlike the process described in FIG. 4, the model of surgical instrument 20 is only displayed with a new position and orientation, at step S526, if all of the criteria in steps S520-524 are met. If any of the criteria in steps S520-524 are not met, the model of surgical instrument 20 continues to be displayed in the existing position and orientation and the process returns to step S518 where workstation 40 receives further user inputs indicating a new position. The process cycles through steps S518 through S524 until an unencumbered instrument path "IP" that is directed toward target "T".

As a result of the cycling through steps S518-S524, workstation 40 only displays the model of surgical instrument 20 at positions and orientations that would provide an unencumbered instrument path "IP" directed toward target "T". Accordingly, the clinician may change the displayed location of the model of surgical instrument 20 by dragging the model of surgical instrument 20, using, for example a touchpad or a mouse, to acceptable unencumbered positions and orientations.

After an unencumbered instrument path "IP" is selected and displayed, workstation 40 may receive, at step S528, a user input indicating that the plan is accepted or rejected. If the user input indicates that the instrument path "IP" is rejected or if no user input is received, the process returns to step S518 and a user may input a new instrument path "IP". If instrument path "IP" is accepted, the process proceeds to step S530 wherein instrument path "IP" is displayed on display 606. Once instrument path "IP" is displayed, the planning process is complete and the clinician may follow the displayed path to the target "T" and conduct the surgical procedure.

Referring now to FIG. 6, there is shown a system diagram of workstation 40. Workstation 40 may include memory 602, processor 604, display 606, network interface 608, input device 610, and/or output module 612. Memory 602 includes any non-transitory computer-readable storage media for storing data and/or software that is executable by processor 604 and which controls the operation of workstation 40. In an embodiment, memory 602 may include one or more solid-state storage devices such as flash memory chips. Alternatively or in addition to the one or more solid-state storage devices, memory 602 may include one or more mass storage devices connected to the processor 604 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 604. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 40.

Memory 602 may store application 42 and/or CT data 214. Application 42 may, when executed by processor 604, cause display 606 to present user interface 616. Network interface 608 may be configured to connect to a network such as a local area network (LAN) consisting of a wired network and/or a wireless network, a wide area network (WAN), a wireless mobile network, a Bluetooth network, and/or the internet. Input device 610 may be any device by means of which a clinician may interact with workstation 40, such as, for example, a mouse, keyboard, foot pedal, touch screen, and/or voice interface. Output module 612 may include any connectivity port or bus, such as, for example, parallel ports, serial ports, universal serial busses (USB), or any other similar connectivity port known to those skilled in the art.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

Specifically, while embodiments of the disclosure have been described with respect to a CT scanner, it is not intended that the disclosure be limited thereto. The current disclosure contemplates use of the systems and methods described herein to plan a path to a target that avoids obstructions that may be present during the performance of various surgical procedures. Those skilled in the art would envision numerous other obstructions. Therefore, the above use of a CT scanner as an example obstruction should not be construed as limiting, but merely as exemplifying particular embodiments.

Detailed embodiments of such devices, systems incorporating such devices, and methods using the same are described above. However, these detailed embodiments are merely examples of the disclosure, which may be embodied in various forms. Therefore, specific structural and functional details disclosed herein are not to be interpreted as limiting but merely as a basis for the claims and as a representative basis for allowing one skilled in the art to variously employ the present disclosure in virtually any appropriately detailed structure.

Embodiments of the presently disclosed surgical planning system and methods thereof are described above in detail with reference to the drawings, in which like reference numerals designate identical or corresponding elements in each of the several views. As used herein, the term "distal" refers to that portion of the surgical instrument that is further from the clinician (e.g. the distal tip of a needle), while the term "proximal" refers to that portion of the surgical instrument that is closer to the clinician (e.g. the proximal handle of a needle). As used herein, the term "clinician" refers to a doctor (e.g. surgeon, radiologist, oncologist, etc.), nurse, technician, or other care provider and may include support personnel. In the above description, well-known functions or construction may not be described in detail to avoid obscuring the present disclosure in unnecessary detail.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended hereto.

What is claimed is:

1. A method of planning a path for a surgical instrument for use during a surgical procedure, the method comprising:
   generating a model of a portion of a patient from images of the patient;
   identifying a target in the images of the patient or the model of the portion of the patient;
   determining dimensions of the patient;
   determining dimensions of the surgical instrument configured to be used during the surgical procedure;

determining dimensions of a bore, defined by an external obstruction, the external obstruction being an object external to the patient's body that interferes with one or more potential paths of the surgical instrument;

determining a location of the bore relative to the patient;

determining dimensions of a clinician's hand;

determining a path for guiding the surgical instrument to the target during the surgical procedure prior to moving the patient through the bore, the path being determined such that the surgical instrument avoids the external obstruction as the patient is moved through the bore and provides sufficient clearance for the clinician's hand to grasp the surgical instrument while the patient is positioned within the bore, the path determined based on the determined dimensions of the surgical instrument, the determined dimensions of the external obstruction, the determined dimensions of the clinician's hand, and a position of the target relative to the patient; and displaying the determined path on a display.

2. The method according to claim 1, further comprising: scanning the patient with at least one of a CT scanner or an MRI scanner to generate the images of the patient.

3. The method according to claim 1, wherein the external obstruction is a CT scanner.

4. The method according to claim 1, wherein determining dimensions of the surgical instrument includes determining dimensions of cables coupled to the surgical instrument.

5. The method according to claim 1, further comprising:
performing dosimetry simulation for the clinician's hand along the planned path; and
displaying results of the dosimetry simulation.

6. The method according to claim 1, wherein determining dimensions of a clinician's hand includes at least one of receiving a user entered glove size, receiving user entered hand dimensions, or imaging the clinician's hand.

7. The method according to claim 1, further comprising: displaying the model of the patient on the display.

8. The method according to claim 7, further comprising: displaying the path on the display superimposed in the model of the patient.

9. The method according to claim 8, further comprising:
imaging the patient during the procedure with the surgical instrument at least partially inserted into the patient; and
displaying a location of the surgical instrument on the display superimposed over the model of the patient and the displayed path.

10. The method according to claim 7, further comprising:
generating a model of the external obstruction from the dimensions of the external obstruction; and
displaying the model of the external obstruction relative to the model of the patient on the display.

11. The method according to claim 7, further comprising:
generating a model of the surgical instrument from the dimensions of the surgical instrument; and
displaying the model of the surgical instrument on the display.

12. The method according to claim 11, further comprising:
receiving a user input instructing a change in at least one of a location or an orientation of the model of the surgical instrument; and
displaying a projected path from the model of the surgical instrument according to the location or the orientation of the displayed model of the surgical instrument.

13. The method according to claim 12, further comprising:
receiving a user input accepting the location or the orientation of the model of the surgical instrument,
wherein the path is further planned according to the location or the orientation of the model of the surgical instrument accepted by the user.

14. The method according to claim 12, further comprising:
displaying the model of the surgical instrument on the display according to the user input instructing the change in at least one of the location or the orientation of the model of the surgical instrument, if determining the instrument path for the surgical instrument to the target during the surgical procedure such that the surgical instrument avoids the external obstruction can be performed according to the user instructed location or orientation of the model of the surgical instrument.

15. The method according to claim 12, further comprising:
displaying the model of the surgical instrument on the display according to the user input instructing the change in at least one of the location or the orientation of the model of the surgical instrument.

16. The method according to claim 12, further comprising:
generating a warning, if determining the instrument path to guide the surgical instrument to the target during the surgical procedure such that the surgical instrument avoids the external obstruction cannot be performed according to the user input instructing the change in at least one of the location or the orientation of the model of the surgical instrument.

17. The method according to claim 12, further comprising:
modifying the user instructed location and orientation of the model, if determining the instrument path to guide the surgical instrument to the target during the surgical procedure such that the surgical instrument avoids the external obstruction cannot be performed according to the user input instructing the change in at least one of the location or the orientation of the model of the surgical instrument.

18. The method according to claim 1, wherein the surgical instrument includes a handle and a shaft, the method further comprising:
determining whether the shaft can reach the target while the handle remains outside of the patient.

19. The method according to claim 1, wherein determining dimensions of the surgical instrument includes reading one of a coded resistor, data stored on a ROM, a bar code, or an RFID tag associated with the surgical instrument.

20. A method of planning a path for a surgical instrument for use during a surgical procedure, the method comprising:
determining dimensions of a patient;
determining dimensions of the surgical instrument configured to be used during the surgical procedure;
determining dimensions of a bore, defined by an external obstruction, the external obstruction being an object external to the patient's body that interferes with one or more potential paths of the surgical instrument;
determining a location of the bore relative to the patient;
determining a path for guiding the surgical instrument to a target during the surgical procedure prior to moving the patient through the bore, the path being determined such that the surgical instrument avoids the external obstruction as the patient is moved through the bore and provides sufficient clearance for a clinician's hand to grasp the surgical instrument while the patient is positioned within the bore, the path determined based on the determined dimensions of the surgical instrument, the determined dimensions of the external obstruction, dimensions of the clinician's hand, and a position of the target relative to the patient; and
displaying the determined path relative to a model of a portion of the patient on a display.

* * * * *